(12) United States Patent
Lenz

(10) Patent No.: US 6,351,690 B1
(45) Date of Patent: Feb. 26, 2002

(54) AUTOMATED METHOD AND SYSTEM FOR PERFORMING ANTIVIRAL DRUG SUSCEPTIBILITY AND RESISTANCE TESTING

(75) Inventor: Steven J. Lenz, Oakland, CA (US)

(73) Assignee: Virologic, Inc., S. San Francisco, CA (US)

( * ) Notice: Subject to any disclaimer, the term of this patent is extended or adjusted under 35 U.S.C. 154(b) by 0 days.

(21) Appl. No.: 09/489,221

(22) Filed: Jan. 21, 2000

(51) Int. Cl.$^7$ ............................................... G06F 19/00
(52) U.S. Cl. ..................... 700/245; 435/6; 435/320.1; 435/369; 435/463; 435/468; 435/91.41; 435/91.52; 435/477; 422/99; 422/100; 422/104; 536/23.5; 536/23.7
(58) Field of Search ............................. 700/245; 435/6, 435/320.1, 369, 463, 468, 91.41, 91.52, 477; 422/99, 100, 104; 536/23.5, 23.7

(56) References Cited

U.S. PATENT DOCUMENTS

| 5,837,464 A | | 11/1998 | Capon et al. | |
|---|---|---|---|---|
| 6,132,685 A | * | 10/2000 | Kercso et al. | 422/104 |
| 6,190,617 B1 | * | 2/2001 | Clark et al. | 422/104 |
| 6,231,813 B1 | * | 5/2001 | Ally et al. | 422/100 |
| 6,242,211 B1 | * | 6/2001 | Peterson et al. | 435/41 |
| 2001/0005489 A1 | * | 6/2001 | Roach et al. | 422/99 |

FOREIGN PATENT DOCUMENTS

WO   WO-97/26539   *   7/1997

OTHER PUBLICATIONS

Huang et al., Drug infusion for control of blood pressure during anesthesia, 2000, IEEE, pp. 3488–3492.*

Weaver, Electroporation of cells and tissues, 2000, IEEE, pp. 24–33.*

Huang et al., Multiple–drug hemodynamic control using fuzzy decision theory, 1998, IEEE, pp. 213–228.*

Mansour, Self–tuning pole–placement multivariable control of blood pressure for post–operative patients: a model–based study, 1989, IEEE, pp. 13–29.*

Scitec Laboratory Automation and Robotics, Robotic System Proposal & Specifications (1997), "Robotic Concepts: Product Specifications & Typical Applications," Attachment C, pp. 1–28; U.S.A.

Lenz, Steven et al., LAN (Jul. 1996), "CRS Adds A Human Feel To Pharmaceutical Automation," vol. 1, No. 3, pp. 6–9; U.S.A.

Moukheiber, Zina, Forbes (Jan. 26, 1998), "A Hail Of Silver Bullets", pp. 76–81; U.S.A.

* cited by examiner

Primary Examiner—William A. Cuchlinski, Jr.
Assistant Examiner—McDieunel Marc
(74) Attorney, Agent, or Firm—John P. White; Cooper & Dunham LLP

(57) ABSTRACT

A system for performing antiviral drug susceptibility and resistance testing is automated using software and robotics. The system includes a transfection apparatus, an infection apparatus and a plate reading apparatus. One or more of the apparatuses may be automated.

18 Claims, 11 Drawing Sheets

20

AUTOMATED METHOD AND SYSTEM FOR PERFORMING ANTIVIRAL DRUG SUSCEPTIBILITY AND RESISTANCE TESTING

BACKGROUND OF THE INVENTION

This invention relates to performance of antiviral drug susceptibility and resistance tests for identifying effective drug regimens for the treatment of viral infections. More particularly, the invention relates to methods and systems for performing antiviral drug susceptibility and resistance tests using robotics and software.

The term "viral drug susceptibility" is generally understood to be the concentration of an antiviral agent at which a given percentage of viral replication is inhibited (e.g. the $IC_{50}$ for an antiviral agent is the concentration at which 50% of virus replication is inhibited). Thus, a decrease in viral drug susceptibility is the hallmark that a mutant virus for which an antiviral agent is selected is becoming resistant to that antiviral drug. The term "viral drug resistance" is generally defined as a decrease in viral drug susceptibility in a given patient over time. In the clinical context, viral drug resistance is evidenced by the antiviral drug no longer being clinically effective in a patient.

Antiviral drug susceptibility and resistance tests are described in U.S. Pat. No. 5,837,464. A viral resistance assay in accordance with the antiviral drug susceptibility and resistance tests described therein comprises transfection, infection and plate reading steps.

Packaging host cells are plated into microtiter plates containing cell culture medium (e.g., f12:DMEM from Gibco 50:50 with added glutamine and without antibiotics) 48 hours prior to transfection at $2 \times 10^4$ cells per well. "Transfection" as used herein means introducing DNA into a host cell so that the DNA is expressed, whether functionally or otherwise; the DNA may also replicate either as an extrachromosomal element or by chromosomal integration. One method which may be used for transformation of the packaging host cells is the calcium phosphate co-precipitation method of Graham and van der Eb (1973) Virology 52, 456–457. Alternative methods for transfection which may be used include the DEAE-dextran method, lipofection and biolistics as described in, for example, Kriegler (1990) Gene Transfer and Expression: A Laboratory Manual (Stockton Press).

In the calcium phosphate co-precipitation method, 5 to 10 mg each of the resistance test vector and the appropriate packaging expression vector(s), 100 microliters of 1M Calcium chloride and phosphate-buffered saline (PBS) are mixed to produce a precipitate. This precipitate is then added to the appropriate wells containing packaging host cells to produce resistance test vector host cells. The protease inhibitor drug(s) or medium is added to individual wells of the microtiter plate that contains packaging host cells at the time of their transfection, at an appropriate range of concentrations. Cell culture medium is added to wells to which drugs have not been added. The plates are lidded and the lidded, package host cell plates are placed in an incubator at 7% CO2, 37° C. and 95% relative humidity for 24 to 48 hours.

Target host cell plates are made 24 hours prior to infection by adding $1.0 \times 10^5$ of cells in cell culture medium into the appropriate wells of a microtiter plate. The plates are lidded, then placed in an incubator at 7% CO2, 37° C. and 95% relative humidity until they are infected. Just prior to infection, the target cell plates are removed from the incubator, the lid is removed and antiviral drugs or cell culture medium is added to the appropriate wells on the plate. The package host cell plates are removed from the incubator and de-lidded. The medium is removed and filtered through a 0.2 micron filter. The resulting viral is added to the appropriate wells in the target host cell plate. The target host cell plate is lidded and placed into an incubator at 7% CO2, 37° C. and 95% relative humidity.

Twenty-four to forty-eight hours later, the target host cell plates are assayed for firefly luciferase activity as described in, for example, Ausubel et al. (1987) Current Protocols in Molecular Biology (Wiley-Interscience). The cell culture medium is removed from the wells, a lyse reagent is added and the plate is incubated at room temperature for 20 minutes. Luciferase substrate is added to the plate and the plate is read by a luminometer to determine the light output.

The antiviral drugs being added to the host cell plates are added at selected times depending upon the target of the antiviral drug. For example, in the case of HIV protease inhibitors, including amprenavir, nelfinavir, saquinavir, ritonavir, and indinavir, they are added to individual plates of packaging host cells at the time of their transfection with a resistance test vector, at an appropriate range of concentrations. HIV reverse transcriptase inhibitors, including AZT, ddI, ddC, d4T, 3TC. and nevaripine, are added to individual plates of target host cells at the time of infection by the resistance test vector viral particles, at a test concentration. The test concentration is selected from a range of concentrations which is typically between about 0.1 nM and about 100 $\mu$M and more specifically for each of the following drugs: AZT, from about 1 nM to about 5 $\mu$M; ddI, from about 1 nM to about 25 $\mu$M; 3TC, from about 1 nM to about 50 $\mu$M; d4T, from about 1 nM to about 25 $\mu$M; and nevaripine, from about 1 nM to about 100 $\mu$M.

Instrumentation for transfecting and infecting cells are known generally in the art, and most practitioners are familiar with the standard resource materials which describe their use and function. However, at present, the tools available to the researcher and clinician for performing antiviral drug susceptibility and resistance tests are inadequate. Manual methods for performing these tests are slow, tedious, and prone to human error. In addition, they are not easy to scale up, provide too low of a throughput for commercialization, and are labor intensive.

SUMMARY OF THE INVENTION

It is an object of this invention to provide automated systems and methods for evaluating the biological effectiveness of candidate drug compounds which act on specific viral genes and/or viral proteins particularly with respect to viral drug resistance and cross resistance.

Another object of this invention is to provide automated systems and methods for performing an assay for identifying and assessing the biological effectiveness of potential therapeutic compounds for treating viral diseases.

Yet another object of this invention is to provide automated systems and methods for performing antiviral drug susceptibility and resistance tests to be used in identifying effective drug regimens for the treatment of viral infections and screening candidate drugs for their capacity to inhibit selected viral sequences and/or viral proteins. The automated performance of the tests may be used for developing, for example, an optimal therapeutic regimen for treatment of HIV/AIDS. The systems and methods in accordance with the present invention may be used to automate the methods of performing drug susceptibility and resistance tests described in, for example, U.S. Pat. No. 5,837,464.

It is another object of this invention to provide automated systems and methods for performing antiviral drug susceptibility and resistance tests which use robotics and software, for example, to introduce a resistance test vector into a host cell, and to determine an expression or inhibition of the indicator gene product in a target host cell in the presence of an antiviral drug.

It is another object of this invention to provide systems and methods for performing the drug susceptibility and resistance test in a safe, standardized, rapid, precise and reliable manner for clinical and research application.

This and other objects of the invention will be apparent from the specification as a whole.

Objects of the present invention may be accomplished by configuring and adapting standard components in a novel manner to produce the following three automated apparatuses for performing the cell assay portion of antiviral drug susceptibility and resistance testing:

1) a Transfection Apparatus which may comprise
   a) track-mounted robotic arm and controller,
   b) robotic-friendly incubator,
   c) automated high density storage unit,
   d) two liquid handlers,
   e) plate lid/de-lid station,
   f) plate aspiration device,
   g) barcode reader,
   h) barcode label printer and application module,
   i) HEPA air supply,
   j) refrigerated hotels,
   k) slave computer,
   l) host computer and customized system control software, and
   m) input/output interface box;

2) an Infection Apparatus which may comprise
   a) track-mounted robotic arm and controller,
   b) robotic-friendly incubator,
   c) two automated high density storage units,
   d) 96-channel pipettor,
   e) plate lid/de-lid station,
   f) plate filtration device,
   g) barcode reader,
   h) barcode label printer and application module,
   i) HEPA air supply,
   j) host computer and system control software, and
   k) input/output interface box; and (3) a Plate Reading System which may comprise
   a) track-mounted robotic arm and controller,
   b) two robotic-friendly incubators,
   c) platewasher and dispenser,
   d) reagent dispenser,
   e) plate de-lid station,
   f) plate reader,
   g) barcode reader,
   h) hotel,
   i) host computer and system control software, and
   j) input/output interface box.

The systems and methods in accordance with the present invention provide significant advantages over presently available methods for performing the assay in a safer, more affordable, more rapid and more reliable manner.

BRIEF DESCRIPTION OF THE DRAWINGS

The above and numerous other objectives, features and advantages that may be achieved by the present invention would be more readily understood from the following detailed description by referring to the accompanying drawings wherein.

DETAILED DESCRIPTION OF THE INVENTION

To explain the invention, we describe some embodiments in connection with figures and their supporting descriptions provided below. In the embodiments described below, some commercially available components are used. It should be understood, however, that the scope and spirit of the invention may be applied regardless of whether customized or off-the-shelf components are used.

Figure 1:
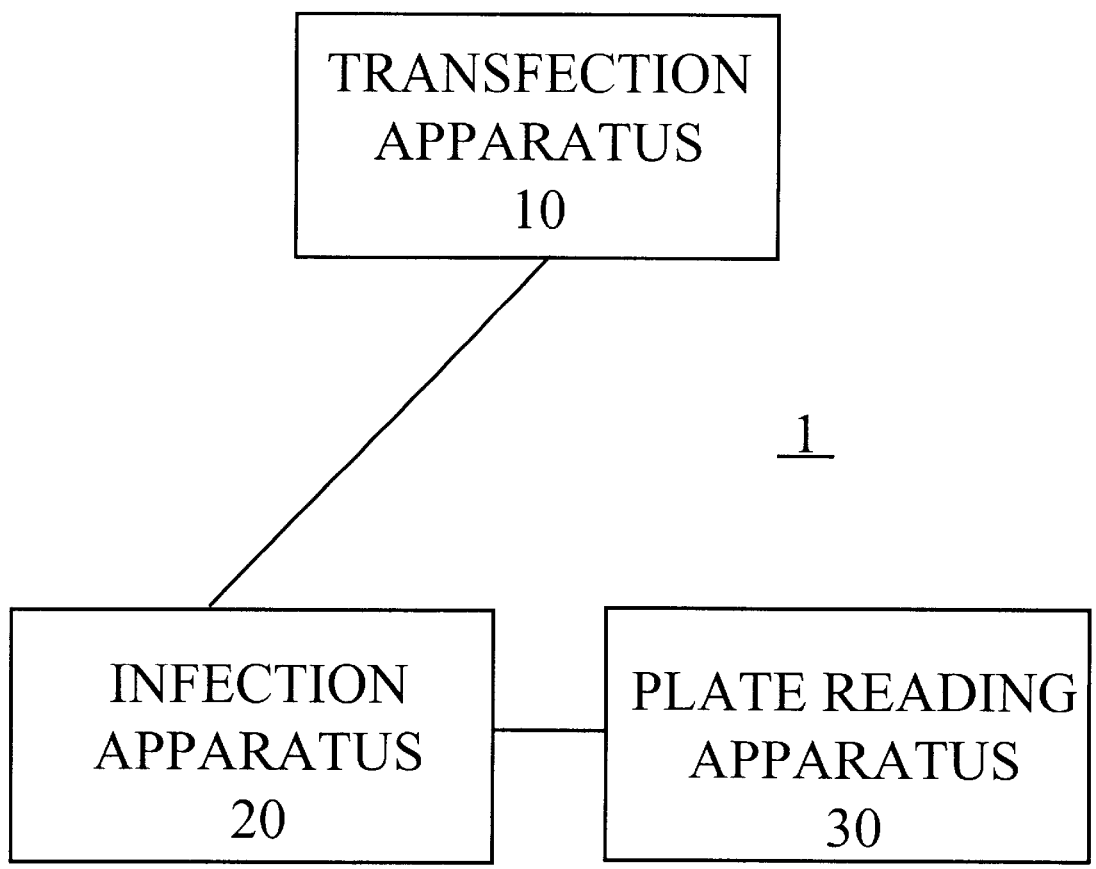
FIG. 1 shows a block diagram of one embodiment of an automated system for performing antiviral drug susceptibility and resistance tests that includes a Transfection Apparatus, an Infection Apparatus and a Plate Reading Apparatus in accordance with the present invention.

The present invention provides a tool for automating antiviral drug susceptibility and resistance tests described, for example, in U.S. Pat. No. 5,837,464, which is hereby incorporated by reference into this application. In accordance with the present invention, an automated system for performing the transfection, infection and plate reading steps of the antiviral drug susceptibility and resistance tests may comprise automation, by use of software and robotics, any one or more of a Transfection Apparatus, an Infection Apparatus and a Plate Reading Apparatus, as described in detail herein below. In accordance with the present invention, FIG. 1 shows automated system 1 comprising Transfection Apparatus 10, Infection Apparatus 20 and Plate Reading Apparatus 30.

The Transfection Apparatus prepares plates for generating viral supernatants to be used in the Infection Apparatus. The system labels each of these plates with a corresponding bar code containing a unique identifier for the sample and the identity of the of the drugs to be tested using the plate.

The Infection Apparatus reads the barcode from the plate, determines the appropriate drugs to be tested, harvests the viral supernatant, adds an aliquot of viral supernatant to a fresh cell plate, and then adds drugs to the plate. The system labels each plate with a bar code containing a unique identifier for the sample, identity of the drugs tested and a replicate number. The Plate Reading Apparatus process and read the infected plates to determine the activity of the tested drug.

Transfection Apparatus

Figure 2A:
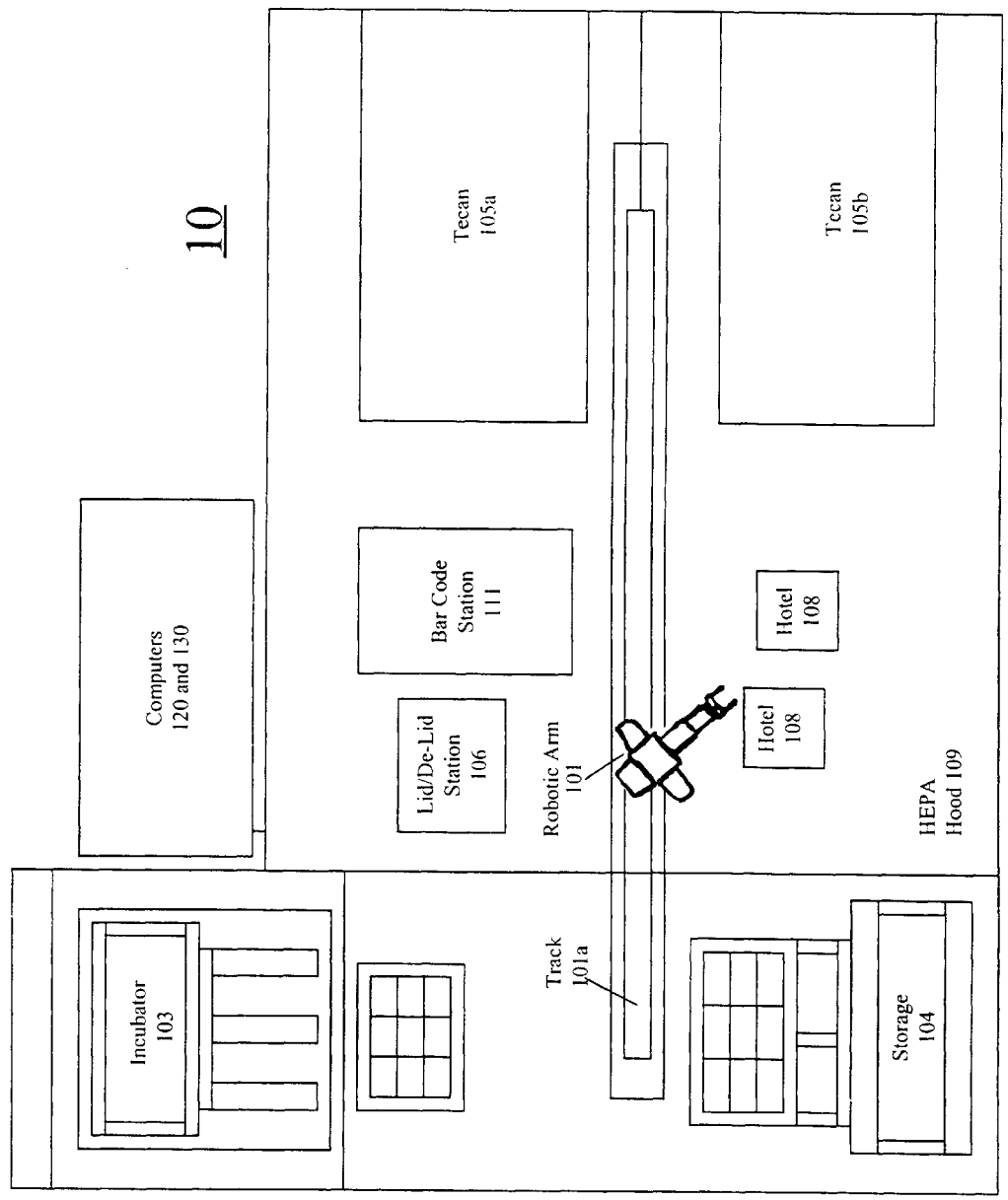
FIG. 2A shows a diagrammatic representation of one embodiment of an automated Transfection Apparatus in accordance with the present invention.
Figure 2B:
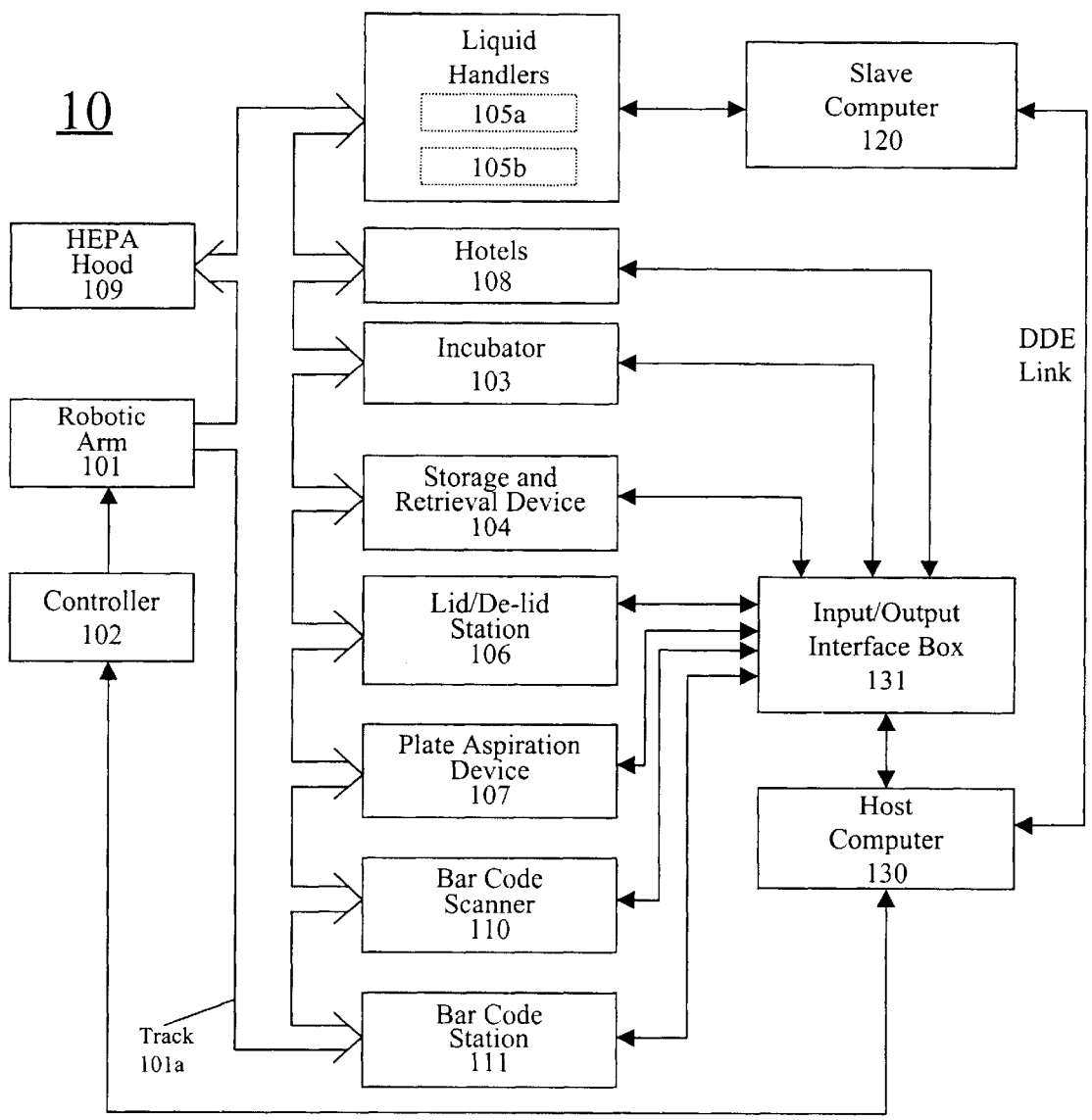
FIG. 2B shows a block diagram of the Transfection Apparatus shown in FIG. 2A.

One embodiment of a Transfection Apparatus in accordance with the present invention is shown in FIGS. 2A and 2B. Transfection Apparatus 10 comprises robotic arm 101 mounted on track 101a, controller 102 for positioning the robotic arm, cell plate incubator 103, automated storage and retrieval device 104, two liquid handlers 105a and 105b, plate lid/de-lid station 106, plate aspiration device 107, refrigerated hotels 108, HEPA canopy 109, bar code reader 110, bar code station 111, slave computer 120, host computer 130 and input/output interface box 131.

Off-the-shelf components may be used in Transfection Apparatus 10 to the extent available. For example, robotic arm 101 may be a CRS Robotics A265 robotic arm equipped with a servo gripper fitted with custom plate gripping fingers mounted on a 3 meter CRS Robotics T265 Linear Track, and CRS Robotics C500 Controller executing RAPL software may be used to position the robotic arm. Other commercially available robotic arms (and controllers) may be used. For example, the ORCA is available from Hewlett Packard. Gantry XYZ systems alternatively may be used. The main requirement is that the robotic arm under the command of controller 102 can transport samples (i.e. plates) between stations/devices.

Cell plate incubator 103 is preferably high capacity and robotics friendly. Such a cell plate incubator capable of holding 450 microtiter plates and maintaining an environment of 7% $CO_2$, 37° C. and 95% relative humidity is available from Scitec Laboratory Automation and Robotics. The incubator may be modified to include an automated stacker and a robotic door for access to one shelf at a time, in order to minimize air exchange for continuous robot access. The shelves of the incubator may be adjustable to accommodate deep wells. Sensors may be located on the robotic access door to indicate when the door is open or closed, on a shuttle mechanism of the automatic stacker to indicate when the shuttle is extended into the incubator chamber, and on an elevator of the automatic stacker for determining if the shelf has been removed or returned to the incubator's internal storage device. The host computer detects the state of the sensors to determine if all of the devices are in the proper state prior to executing a command to interact with the incubator.

Storage and retrieval device 104 for storing tips preferably is high density. It may have, for example, a 180 tip box capacity. The storage device may have several vertically-stacked shelves, with adjustable spacing between the shelves to accommodate deep well. The device may have optionally a robotic pick-up window and an elevator for providing random access to all the shelves, allowing any shelf to be delivered to the pick-up window. Sensors may be located on the elevator and on a shuttle mechanism of storage device 104 for removing or returning a shelf to the storage device. The host computer detects the state of the sensors to determine if the shelf has been successfully removed or returned prior to executing a command to interact with the storage device.

Liquid handlers 105a and 105b each may have multiple pipetting tips, a disposable tip option, customized tip disposal unit and customized plate locators. The Tecan Genesis Model 150/8 Combination Tip RSP liquid handlers may be used. The liquid handlers are controlled remotely via software running locally and on slave computer 120.

Plate lid/de-lid station 106 may be a six position vacuum activated lid/de-lid station available from Scitec Laboratory Automation and Robotics.

Operation of the lid/de-lid station may be as follows exemplarily. The robotic arm positions a plate under a vacuum port of the station. The host computer actuates a valve of the station to pull a vacuum on the port which secures the lid to the port. The robotic arm lowers the plate from the port while leaving the lid behind. In order to replace the lid on the plate, the robotic arm positions the plate under the port which has the lid secured to it. The valve is deactivated and the lid is released onto the plate. A sensor on the valve indicates the presence and absence of a vacuum. The host computer detects the state of the sensor to determine if the lid was properly removed or replaced.

Plate aspiration device 107 may be equipped with a multi-channel dispensing manifold and a multi-channel aspiration head. The TiterTek MRD8 Platewasher and Dispenser may be used. The plate aspiration device is controlled by software that executes on the host computer and communicates with the host computer via an RS232c serial port.

Operation of the plate aspiration device may be as follows exemplarily. The robotic arm places a delidded plate on the plate aspiration device. A positioning sensor on the plate aspiration device indicates when a plate is properly positioned. The host computer detects the state of the sensor, and then issues commands to the device to move the plate under the custom aspiration head and aspirate the contents of the well. The process is repeated for each column on the plate. The plate aspiration device signals to the host computer, via the RS232c serial port, that the commands have been successfully completed. The robotic arm detects the state of the positioning sensor, and then removes the aspirated plate from the device.

Refrigerated hotels 108 for storing drugs are temperature controlled and equipped with temperature sensors. The refrigerated hotels comprises shelves enclosed in a water jacketed shell equipped with pneumatically operated doors. A refrigerated circulating bath pumps coolant through the water jacketed shell to cool the unit to the bathes temperature set point.

Operation of the hotels may be as follows exemplarily. The host computer signals the robotic arm to remove a drug container from the hotel. The robotic arm controller activates an air valve to open the doors. The robotic arm controller detects the state of a door sensor to verify that the door is open. The robotic arm removes the container and deactivates the valve to close the doors. The robotic arm controller verifies, via grip sensors on its hand and the state of the door sensor, that a container was successfully retrieved. The controller returns the information to the host computer.

HEPA Filter hood 109 assists in maintaining a sterile environment by supplying fresh air and cover to liquid handlers 105a and 105b, plate aspiration device 107, bar code station 111, and lid/de-lid station 106. The filter hood comprises fans that are manually turned on by the operator prior to starting the system.

Bar code labels may be attached to plates to identify the plates within the system. Thus, the system can track the plates, without the requirement that the plates be placed in any particular order. Bar code scanner 110 may be one commercially available from, for example, Microscan. Bar code station 111 includes a labeler for applying a label onto a plate, if it is not lidded, or onto the lid of a lidded plate. The Sagian Print and Apply Bar Code Labeler station may be used.

Operation of the barcode station may be as follows exemplarily. A host computer controls the barcode station by issuing commands to the device via an RS232c serial port connection. The robotic arm places a plate on the barcode station. The host computer sends a command to apply a barcode on the plate. The barcode content and format is determined by the host computer. The barcode encodes the plate's unique identifier and the drugs to be tested. Application of the barcode is verified by scanning the plate. If it is determined that the label failed to attach, the host computer repeats the barcode label command up to three times.

Slave computer 120 executes software for controlling liquid handlers 105a and 105b. The slave computer reads a work list specifying which sample and which drugs are to be processed, and then executes the appropriate procedure on the liquid handler. The slave computer is connected to the host computer via a Dynamic Data Exchange link.

Host computer 130 provides work scheduling, operator interface and control of the instrumentation. Software running on host computer 130 provides an application development environment, drivers for communicating with each component of the system, including robotic arm 101 and controller 102, and a user interface. The user interface provides the user with means for designing, scheduling, optimizing and monitoring of the execution of the Transfection Apparatus. One such software that may be used on a Windows personal computer platform is Scitec's WinClara Scheduler and Control software and Scitec's ROSCOS software. Host computer 130 communicates via an input/output interface box 131 with incubator 103, storage and retrieval device 104, lid/de-lid station 106, plate aspiration device 107, hotels 108, bar code reader 110 and bar code station 111. Thus, the host computer can control valves, signal lights, switches and sensors in the devices.

Operation of Transfection Apparatus 10 may be controlled by a user via the user interface executing on host computer 130. The operator may enter, for example, any required information, a worklist containing information regarding drugs to be tested, and information regarding a patient derived resistance test vector to be used in the assay. The system may then be initialized via the user interface.

Figure 2C:
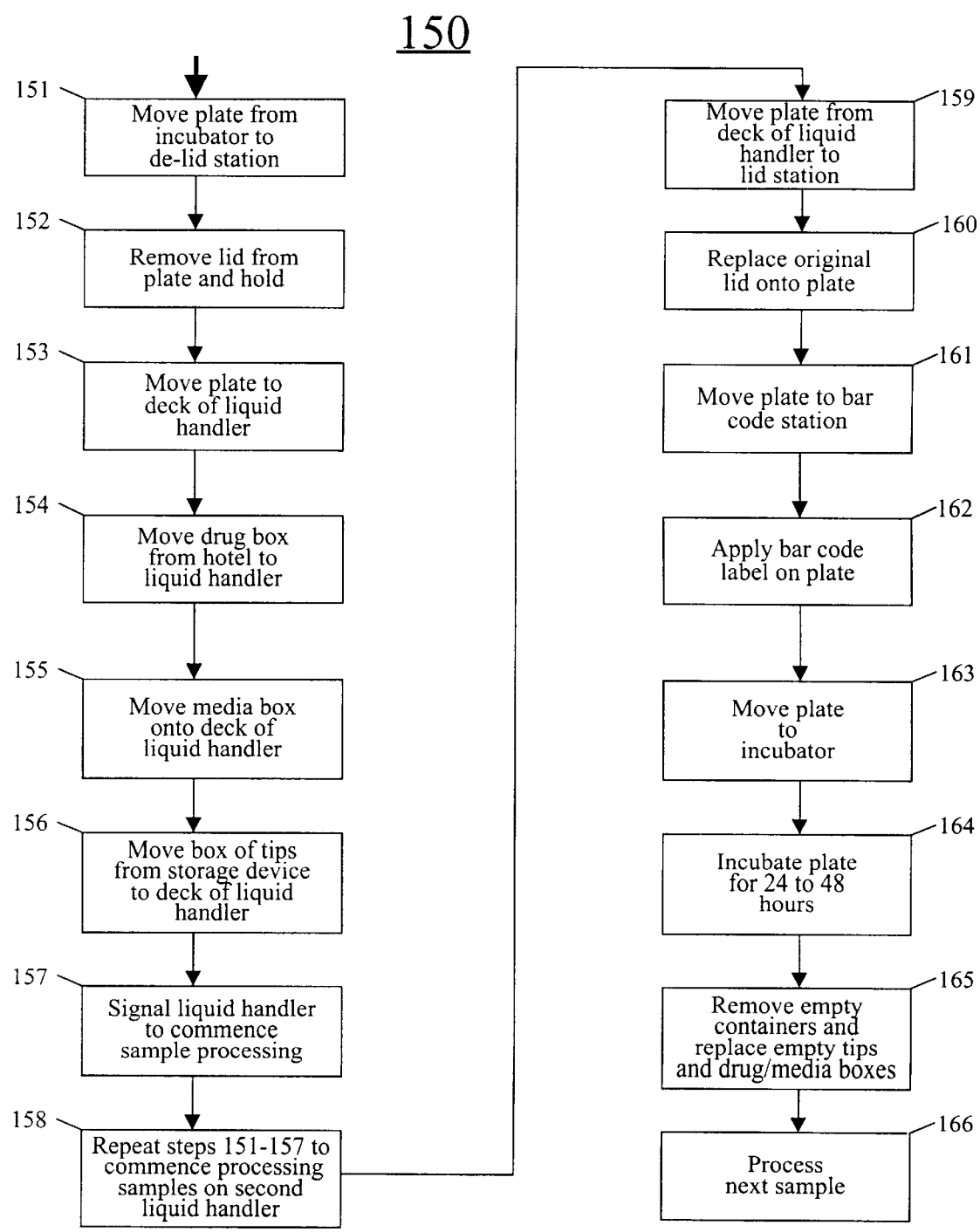
FIG. 2C shows a flow chart of a transfection process performed by the Transfection Apparatus shown in FIG. 2B.

As further described below in connection with FIG. 2C, following initialization, tip boxes are loaded into the storage device 104, followed by loading packaging cell plates into incubator 103 and then placing drug boxes into hotel 108. A plate containing samples is loaded onto the deck of liquid handler 105a, along with a precipitation tube containing the appropriate packaging expression vector(s) and phosphate buffered saline (one tube for each sample) and a reagent container for calcium chloride. Execution of Transfection Apparatus 10 is then started, and continues until all samples have been processed.

A transfection process 150 which is performed by the Transfection Apparatus may include all or a combination of the steps described below in connection with FIG. 2C. The steps may be scheduled in a manner that would be known to one skilled in the art to optimize efficiency, when and as required.

In step 151, robotic arm 101 removes a packaging host cell plate from incubator 103 and delivers it to de-lid station 106 which then removes and holds the lid in step 152. The de-lidded plate is placed onto the deck of liquid handler 105a by robotic arm 101 in step 153. Depending on the drugs to be tested, the process may be repeated for a second plate. This determination is made by evaluating the worklist entries for the sample being processed.

In step 154, robotic arm 101 retrieves a drug box from hotel 108 and places it onto the deck of liquid handler 105a. A media box is retrieved and placed by robotic arm 101 onto the deck of liquid handler 105a in step 155. In step 156, robotic arm 101 retrieves a box of tips from storage device 104 and places it onto the deck of liquid handler 105a. In step 157, host computer 130 signals liquid handler 105a to commence processing the samples.

In step 158, steps 151–157 are repeated to begin processing samples on the second liquid handler 105b.

After the liquid handler has processed the samples, in step 159 robotic arm 101 removes the packaging host cell plate from the deck of the liquid handler and delivers the plate to lid/de-lid station 106. The lid station replaces the original lid of the plate on the plate in step 160.

Robotic arm 101 moves the plate to barcode application station 111 in step 161, and a bar code label is applied to the plate by bar code labeler 111 in step 162. The label contains the unique sample identifier and a unique identifier for any drugs added during transfection.

In step 163, robotic arm 101 returns the plate to incubator 103 which then cultures the plate at 7% $CO_2$, 37° C. and 95% relative humidity for 24 to 48 hours in step 164.

Robotic arm 101 removes any empty containers from liquid handlers 105a and 105b and replaces empty tips and drug or media boxes in step 165, prior to processing the next sample.

Figure 2D:
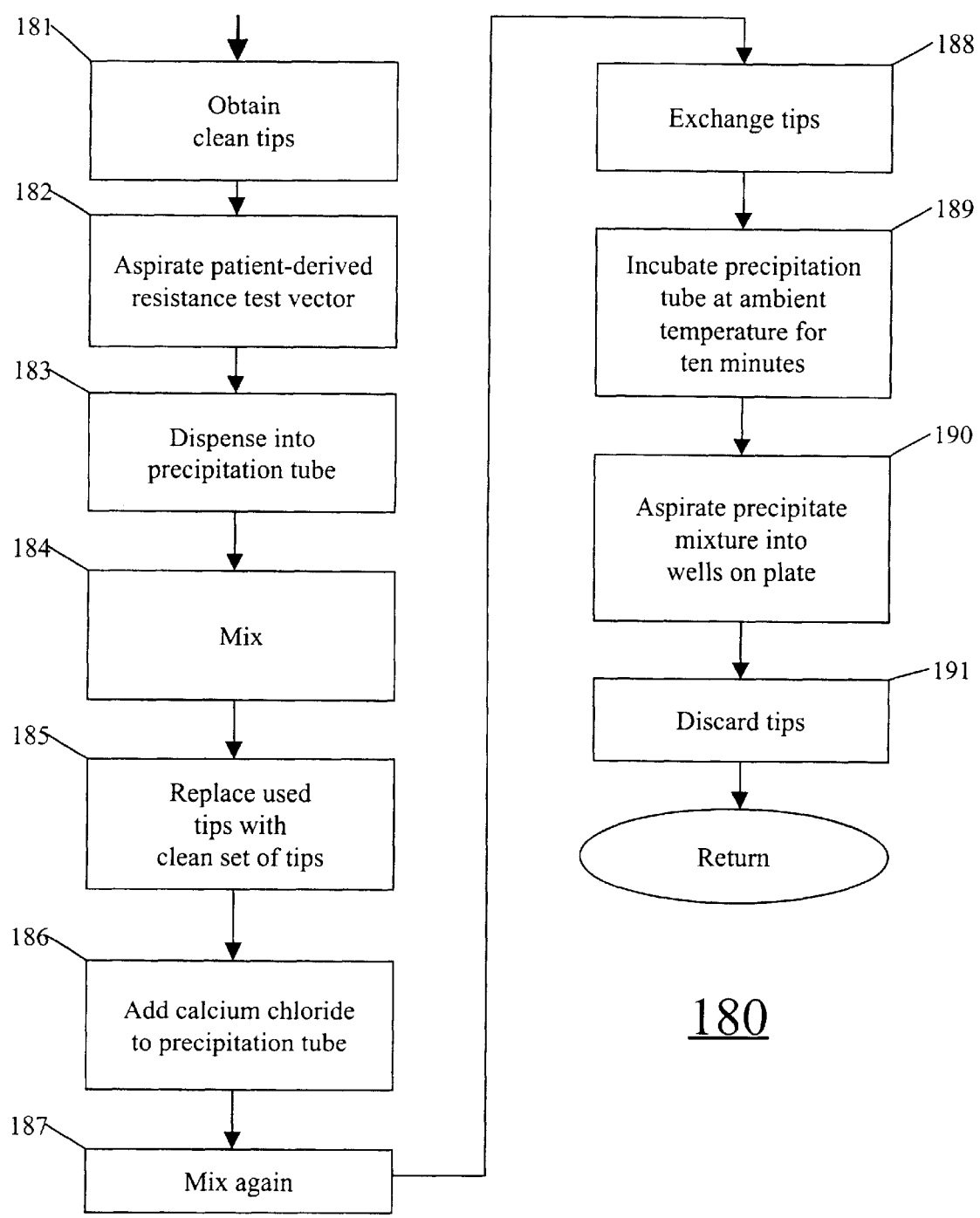
FIG. 2D shows a flow chart of a sample processing method in accordance with the present invention.

Each of the liquid handlers may be programmed to perform a method 180 of sample processing as shown in FIG. 2D.

The liquid handler obtains clean tips in step 181, then aspirates the appropriate volume of patient-derived resistance test vector in step 182, as determined by the work list, and dispenses it into the precipitation tube in step 183, followed by mixing in step 184. The used tips are discarded and replaced with a clean set of tips in step 185.

Calcium chloride is added to the precipitation tube in step 186, followed by additional mixing in step 187 and an exchange of tips in step 188. The precipitation tube is incubated for 10 minutes at ambient temperature in step 189. During incubation step 189, the liquid handler may add drug or media to the appropriate wells on the packaging host cell plate, followed by a tip exchange. Whether drug or media is added is determined using the worklist.

After the incubation in step 189, the liquid handler aspirates a fixed volume of precipitate mixture into the appropriate wells on the plate(s) in step 190 and the tips are discarded in step 191.

The Transfection Apparatus should be configurable by the operator. The number of replicates, the volumes of the samples, use of one or both liquid handlers are each flexible and may be specified by the operator. Volumes for all reagents, the use of disposable tips or fixed tips may be modified without substantial changes to the system's software or hardware. Tracking of samples, bar code and assay parameters may all be specified in a single computer file which can easily be edited. In short, volumes, time, quantity, type of plate, how bar codes are applied and processed each may be altered and indeed expected to be altered as required.

Infection Apparatus

Figure 3A:
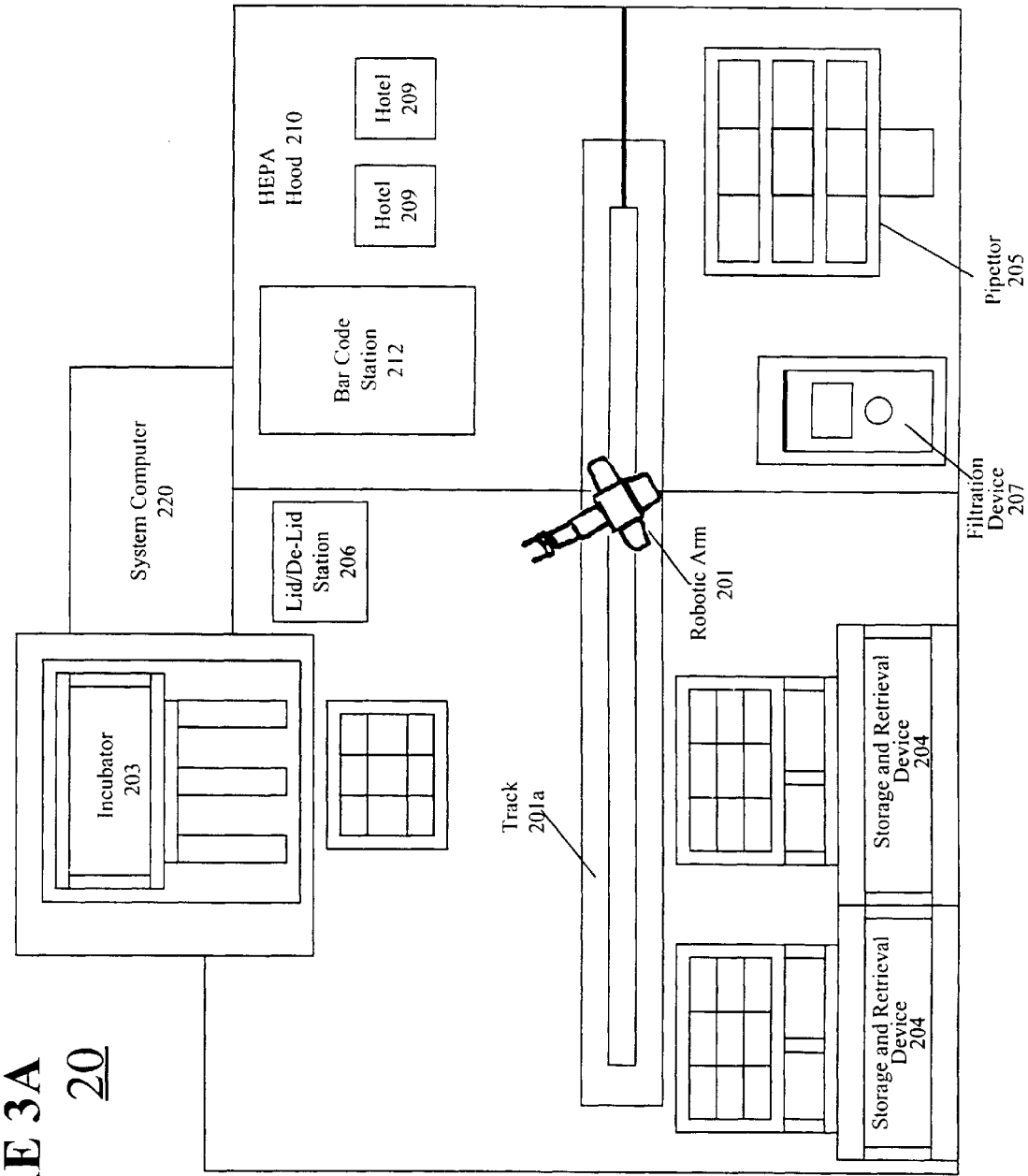
FIG. 3A shows a diagrammatic representation of one embodiment of an automated Infection Apparatus in accordance with the present invention.
Figure 3B:
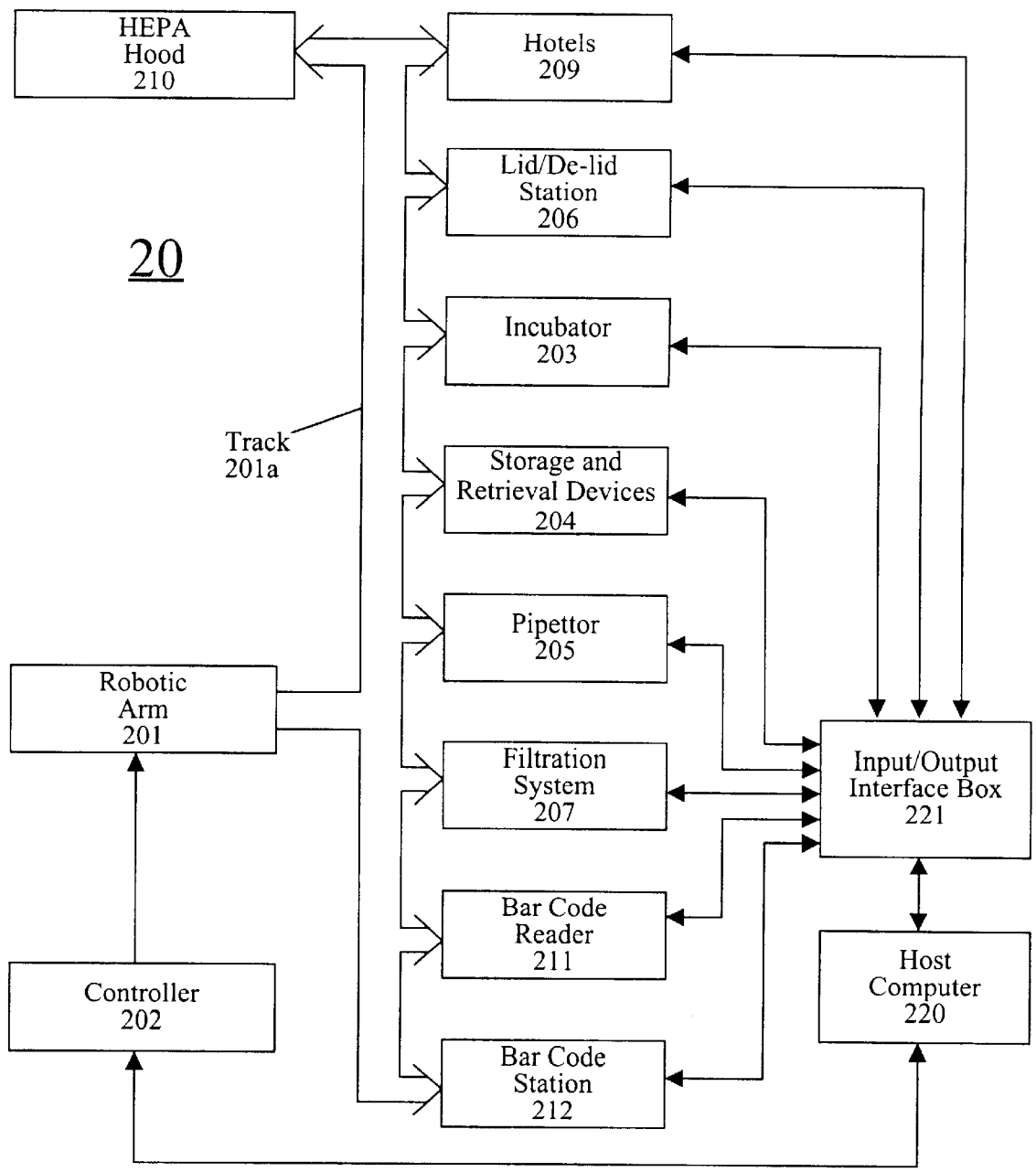
FIG. 3B shows a block diagram of the Infection Apparatus shown in FIG. 3A.

One embodiment of an Infection Apparatus in accordance with the present invention is shown in FIGS. 3A and 3B. Infection Apparatus 20 comprises robotic arm 201 mounted on track 201a, controller 202 for positioning the robotic arm, cell plate incubator 203, automated storage and retrieval devices 204, pipettor 205, plate lid/de-lid station 206, plate filtering device 207, refrigerated hotel 209, HEPA canopy 210, bar code reader 211, print and apply bar code station 212, host computer 220 and input/output interface box 221.

Off-the-shelf components, to the extent available, may be used in the Infection Apparatus. For example, robotic arm 201 may be CRS Robotics A265 robotic arm equipped with a servo gripper fitted with custom plate gripping fingers, mounted on a 3 meter CRS Robotics T265 Linear Track, and controller 202 may be a CRS Robotics C500 Controller executing RAPL software for positioning the robotic arm. The Hewlett-Packard ORCA, a Gantry XYZ system, or other robotic arms alternatively may be used. The main requirement is that the robotic arm under the command of controller 202 can transport plates between stations/devices. Robotic arm 201 and controller 202 may be configured similarly to robotic arm 101 and controller 102, respectively.

Cell plate incubator 203 is preferably high capacity and robotics friendly. Such an incubator capable of holding 450 microtiter plates and maintaining an environment of 7% $CO_2$, 37° C. and 95% relative humidity is available from Scitec Laboratory Automation and Robotics. The incubator may be modified to include an automated stacker and a robotic door for access to one shelf at a time, in order to minimize air exchange for continuous robot access. The shelves of the incubator may be adjustable to accommodate deep wells. Cell plate incubator 203 may be configured similarly to incubator 103.

Automated storage and retrieval devices 204 should be capable of holding plates and boxes of pipette tips at a high density. The storage devices may have several vertically-stacked shelves, with adjustable spacing between the shelves to accommodate deep well. The storage devices may have optionally a robotic pick-up window and an elevator for providing random access to all the shelves, allowing any shelf to be delivered to the pick-up window. Device 204 may be configured similarly to device 104.

Pipettor 205 should provide accurate and flexible pipetting of liquid samples into the plates. For 96-well format plates, the pipettor may be a Cyclone 96-channel pipettor from Scitec which is equipped with a 9 position worktable. The pipetting workstation has high XY resolution. Pipetting workstations for 384-well format plates are commercially available and may be used alternatively. In order to achieve the desired throughput, a tip disposition feature is preferred for the pipetting workstation as well.

Lid/de-lid station 206 may be a six position vacuum activated lid/de-lid station available from Scitec Laboratory Automation and Robotics. Station 206 may be configured similarly to station 106.

Plate filtering device 207 collects filtrates from a filter bottom plate into a microtiter. A Vacuum Filtration Station from Scitec may be used. The plate filtering device has a pneumatically activated collection drawer and vacuum valve for pulling the contents of a filter plate into a collection plate.

Operation of the plate filtering device may be as follows exemplarily. The robotic arm controller opens the collection drawer by activating its valve. The robotic arm sets a collection plate into the drawer, and then deactivates the valve to close the drawer. The robotic arm sets a filter plate onto the filter plate position at the top of the device. The robotic arm controller activates the vacuum valve to pull liquid through the filter and into the collection plate. The robotic arm controller deactivates the vacuum valve. Next, the robotic arm disposes of the filter plate, opens the collection drawer and retrieves the collection plate. Sensors on the vacuum valve and drawer are used to detect whether the device has functioned as expected.

Refrigerated hotels 209 for storing drugs are temperature controlled and equipped with temperature sensors. Hotels 209 may be configured similarly to hotels 108.

HEPA Filter hood 210 assists in maintaining a sterile environment by providing cover and supplying fresh air to pipettor 205, filtration station 207, hotels 209 and bar code station 212. Filter hood 210 may be configured similarly to filter hood 109.

Bar code labels may be attached to plates to identify the plates within the system. Thus, the system can track the plates, without the requirement that the plates be placed in any particular order. Bar code scanner 211 may be one commercially available from, for example, Microscan. Bar code station 212 includes a labeler for applying a label onto a plate, if it is not lidded, or onto the lid of a lidded plate. The Sagian RS232 Controlled Print and Apply Bar Code Labeler Station may be used. Bar code scanner 211 and station 212 may be configured similarly to bar code scanner 110 and station 111.

Host computer 220 provides work scheduling, operator interface and control of the instrumentation. The user interface may include means for designing, scheduling, optimizing and monitoring execution of the Infection Apparatus. Software running on the host computer provides an application development environment, drivers for communicating with each component of the system and a user interface for operating the Infection Apparatus. Commercially available software which may be used on a Windows/personal computer platform includes, for example, Scitec's WinClara Scheduler and Control software, and Scitec's ROSCOS software. Host computer 220 communicates via a Scitec Input/Output Interface box 221 with incubator 203, storage and retrieval devices 204, pipettor 205, filtration system 207, bar code reader 211 and bar code station 212. Thus, the host computer can control valves, signal lights switches sensors in the devices.

Operation of the Infection Apparatus may be controlled by a user via the user interface executing on host computer 220. The operator may enter any required information, and then initialize the system via the user interface. As further described below in connection with FIGS. 3C, after the system is initialized, tip boxes and filter plates (optional) are loaded into storage and retrieval devices 204, followed by loading packaging and target host cell plates into incubator 203 and then placing drug boxes into hotels 209. Execution of the Infection Apparatus is then started, and continues until all samples have been processed.

Figure 3C:
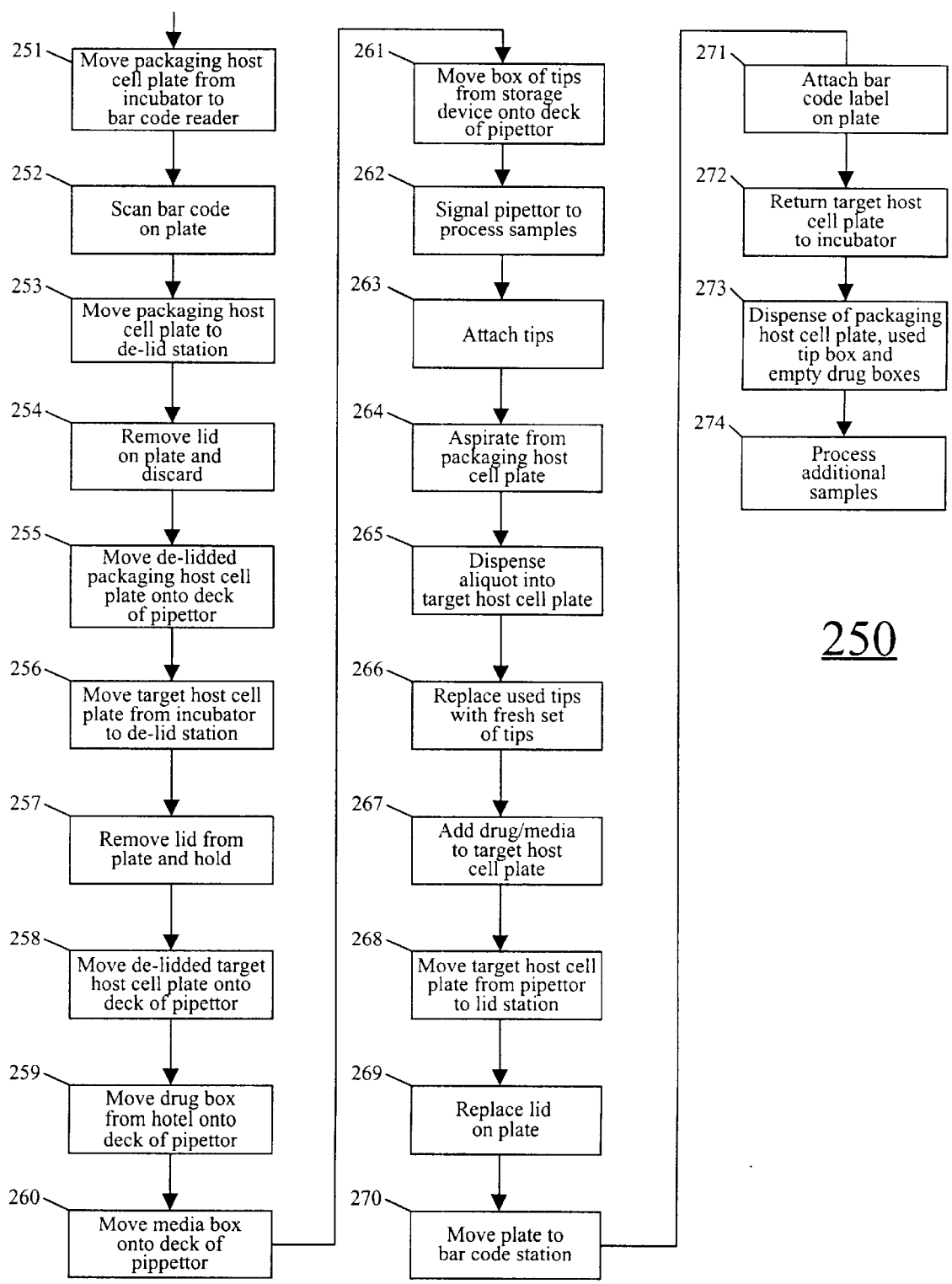
FIG. 3C shows a flow chart of an infection process performed by the Infection Apparatus shown in FIG. 3B.

An infection process 250 which is performed by the Infection Apparatus may include all or a combination of the steps described below in connection with FIG. 3C. The steps may be scheduled in a manner that would be known to one skilled in the art to optimize efficiency, when and as required.

Robotic arm 201 removes a packaging host cell plate from incubator 203 and delivers the plate to bar code reader 211 in step 251. The bar code scanner reads a bar code label on the packaging host cell plate in step 252. The robotic arm then delivers the plate to de-lid station 206 in step 253. The de-lid station removes and discards the lid in step 254. The robotic arm then places the de-lidded packaging host cell plate onto the deck of pipettor 205 in step 255.

Robotic arm 201 removes a target host cell plate from incubator 203 and delivers the plate to de-lid station 206 in step 256. The de-lid station then removes and holds the lid from the target host cell plate in step 257. The de-lidded target host cell plate is then placed onto the deck of pipettor 205 in step 258. Additional target host cell plates may be retrieved based on the number of replicates specified by the operator.

Robotic arm 201 retrieves a drug box from hotels 209 and places it onto the deck of the pipettor 205 in step 259. The robotic arm retrieves a media box and places it onto the deck of the pipettor in step 260. A box of tips is retrieved by the robotic arm from storage devices 204 and placed onto the deck of the pipettor in step 261. Step 261 is repeated three times.

Next, in step 262 host computer 220 signals pipettor 205 to process the samples. The pipettor attaches tips in step 263, aspirates the set volume from the packaging host cell plate in step 264, and then dispenses an aliquot into each of the target host cell plates in step 265. In step 266, the tips are discarded into the waste shoot on the worktable, and a fresh set of tips is attached. Drug or media is added to the target host cell plates in step 267, according to information decoded from the bar code read from the packaging host cell plate.

After the drug or media is added, robotic arm 101 removes the target host cell plate from pipettor 205, and delivers the plate to lid/de-lid station 206 in step 268. The lid station replaces the lid onto the target host cell plate in step 269. The robotic arm then moves the target host cell plate to bar code label application station 212 in step 270. In step 271, bar code labeler 212 attaches a bar code label on the target host cell plate, based on the information read from the packaging host cell plate and its replicate number.

Robotic arm 201 then returns the target host cell plate to its original position in incubator 203 in step 272. In step 273, the robotic arm disposes of the packaging host cell plate, used tip boxes and any empty drug boxes, prior to processing any additional samples in step 274.

The Infection Apparatus may utilize filtration plates. This is accomplished by transferring viral supernatant from the packaging host cell plate to a filter bottom plate after step 255 described above. Robotic arm 201 places a microtiter plate into the collection shelf on filtration device 207, then moves the filter bottom plate into the filter plate position of the filter station 207. A vacuum is applied and the filtrate is collected in the microtiter plate. The robotic arm then places the microtiter plate on pipettor 205 and the filter bottom plate is discarded. The process continues at step 256 described above.

The Infection Apparatus may track plates by bar code. There is no need to place the packaging plates in any particular order. A processing log is automatically generated which specifies when and how tasks were performed, any errors that occurred and operator information required for validation of the system in a regulated environment.

The Infection Apparatus may be equipped with remote access via a modem or web browser for monitoring system status. A signaling light changes color based on the status; red denotes an error, yellow denotes the system is processing samples and green means the system is idle. The system may also have dial out functionality for contacting the operator via pager and/or e-mail in the case of an error.

All parameters such as whether or not to use filter plates, types and number of plates or drug boxes and exchange of tips are configurable by the operator without substantial changes to the system's hardware or software.

Plate Reading Apparatus

Figure 4A:
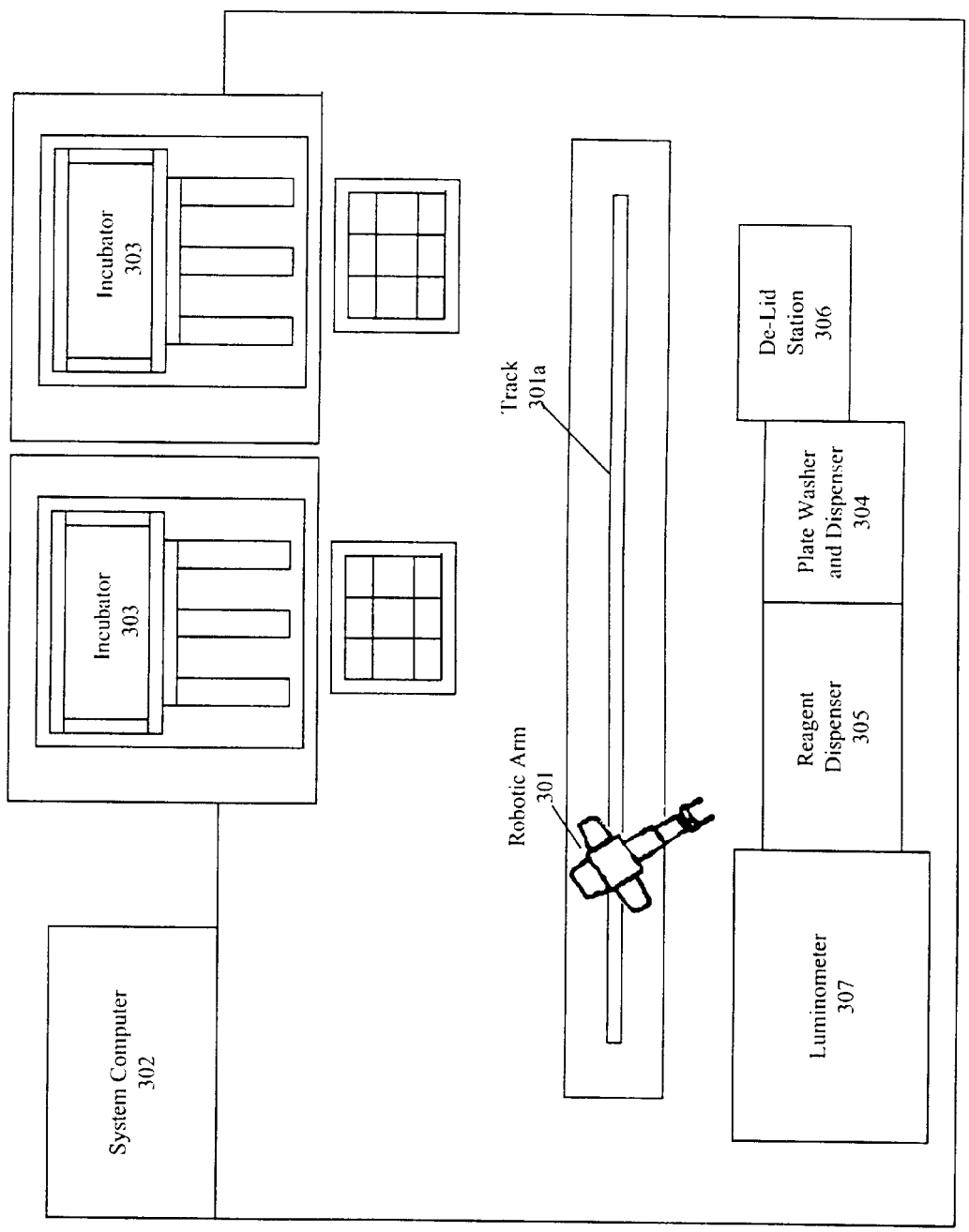
FIG. 4A shows a diagrammatic representation of one embodiment of an automated Plate Reading Apparatus in accordance with the present invention.
Figure 4B:
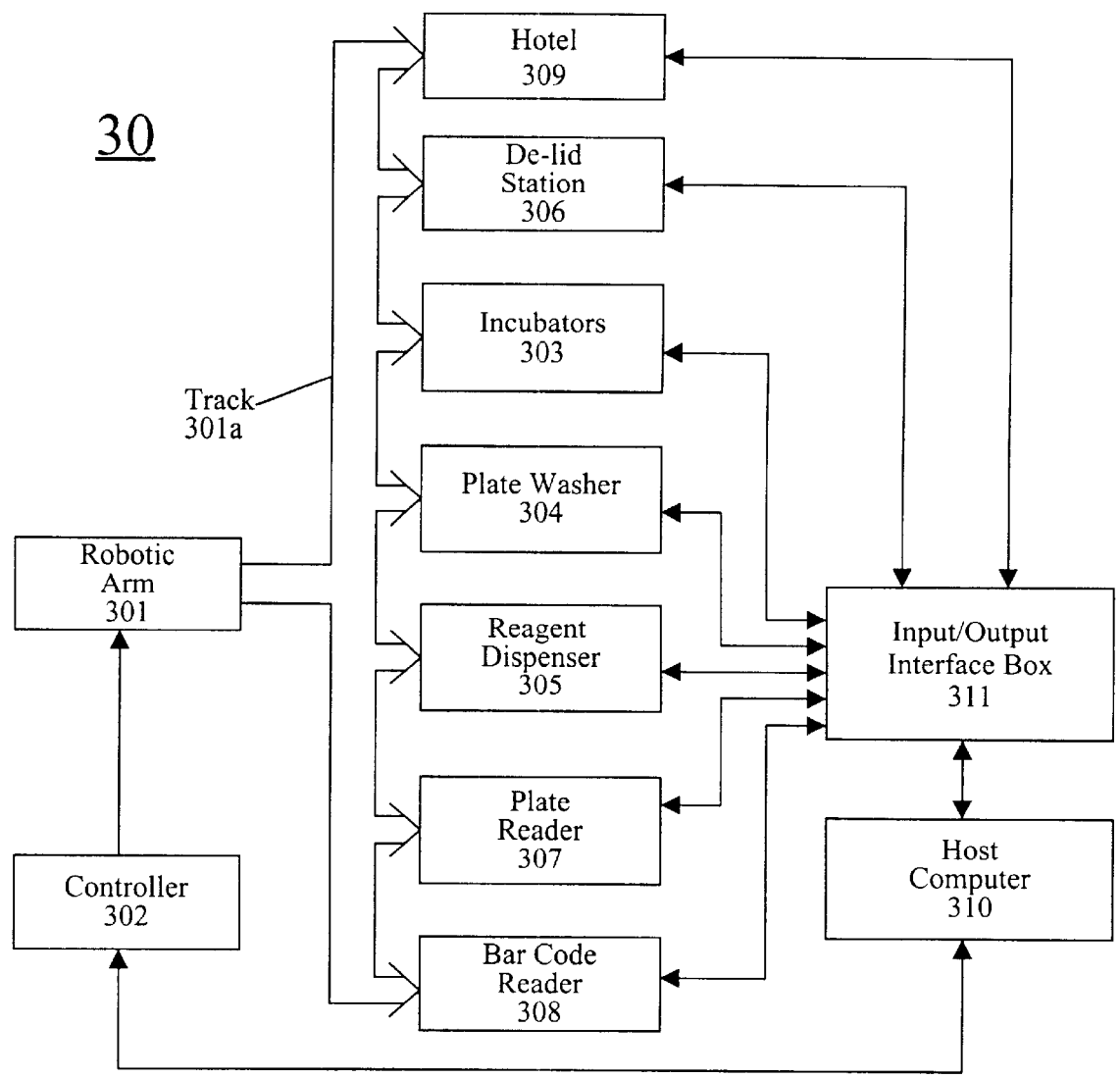
FIG. 4B shows a block diagram of one embodiment of the Plate Reading Apparatus shown in FIG. 4A.

One embodiment of a Plate Reading Apparatus in accordance with the present invention is shown in FIGS. 4A and 4B. Plate Reading Apparatus 30 comprises robotic arm 301 mounted on track 101a, controller 302 for positioning the robotic arm, cell plate incubators 303, platewasher and dispenser 304, reagent dispenser 305, plate de-lid station 306, plate reader 307, bar code reader 308, hotel 309, host computer 310 and input/output interface box 311.

Off-the-shelf components, if available, may be used in Plate Reading Apparatus 30. For example, robotic arm 301 may be a CRS Robotics A265 robotic arm equipped with a servo gripper fitted with custom plate gripping fingers and mounted on a 3 meter CRS Robotics T265 Linear Track, and controller 302 may be a CRS Robotics C500 Controller executing RAPL software for positioning the robotic arm. Commercially available robotic arms may be obtained alternatively from Mitsubishi, Hewlett-Packard, amongst others. The main requirement is that the robotic arm under the control of controller 302 can transfer plates between stations/devices. Robotic arm 301 and controller 302 may be configured similarly to robotic arm 101 and controller 102, respectively, and to robotic arm 201 and controller 202, respectively.

Cell plate incubators 303 are preferably high capacity and robotics friendly. The incubators may include an automated stacker and a robotic door for access to one shelf at a time, in order to minimize air exchange for continuous robot access. The shelves of the incubators may be adjustable to accommodate deep wells. Such incubators capable of holding 450 microtiter plates and maintaining an environment of 7% $CO_2$, 37° C. and 95% relative humidity are available from Scitec Laboratory Automation and Robotics. Cell plate incubator 303 may be configured similarly to incubator 103 and to incubator 203.

Platewasher and dispenser 304 may include a multi-channel dispensing manifold and a multi-channel aspiration head. A commercially available platewasher and dispenser such as the TiterTek MRD8 Platewasher and Dispenser may be used. The plate aspiration device 304 is controlled by software that executes on the host computer and communicates with the host computer via an RS232c serial port. The plate aspiration device is equipped with a customized aspiration head to allow gentle and complete aspiration of well contents.

Operation of the plate aspiration device may be as follows exemplarily. The robotic arm places a delidded plate on the plate aspiration device. A positioning sensor on the device indicates when a plate is properly positioned. The host computer detects the state of the sensor, and then issues commands to the device to move the plate under the custom aspiration head and then aspirate the contents of the well. The process is repeated for each column on the plate. The device signals to host computer, via the RS232c serial port, that the commands have been successfully completed. The robotic arm detects the state of the positioning sensor then removes the aspirated plate from the device.

Reagent dispenser 305 may include a syringe module and accommodate 96 well plates as well as 384 well plates. The dispenser also may have multi-tip manifolds for dispensing simultaneously to multiple wells. The Scitec Automated Reagent Dispenser System equipped with a Cavro XL 3008 pump, eight 250 milliliter syringes and reagent manifold block capable of dispensing to 24 wells simultaneously may be used.

De-lid station 306 may be a single position vacuum activated de-lid station from Scitec Laboratory Automation and Robotics.

Plate reader 307 preferably has a robotic friendly plate holder.

A Wallac Victor$^2$ 1420 Multilabel Counter may be used as the luminometer. The Victor is preferred because it doesn't require a cooling unit.

Operation of the plate reader may be as follows exemplarily. The robotic arm places a delidded plate into the shuttle device on the Victor. The host computer sets the plate reading protocol and sends the read plate command via a custom Victor control application. The Victor transmits the results back to the host computer for final formatting and storage. The custom application utilizes the Victor's internal diagnostics to determine if the plate was successfully read.

Bar code scanner 308 may be one commercially available from, for example, Microscan.

Microplate hotel 309 stores plates at ambient temperature. Hotel 309 may have temperature sensors. The hotel comprises a series of shelves that are equally spaced. The shelves are large enough to hold the plate and wide enough to allow the robotic arm to retrieve plates from the shelves.

Host computer 310 provides for work scheduling, operator interface, control of the instrumentation and data acquisition. Software running on host computer 310 provides an application development environment, drivers for communicating with each component of the system and a user interface for operating the Plate Reading Apparatus. The user interface may provide means for designing, scheduling, optimizing and monitoring execution of the Plate Reading Apparatus. Commercially available software which may be used include, for example, Scitec's WinClara Scheduler and Control software, and Scitec's ROSCOS software. Host Computer 310 communicates via input/output interface box 311 with incubators 303, platewasher 304, reagent dispenser 305, plate reader 307 and bar code reader 308. Thus, the host computer can control valves, signal lights, switches and sensors in the devices.

Operation of the Plate Reading Apparatus may be controlled by the user via the user interface executing on host computer 310. The operator may enter any required information and then initialize the system via the user interface.

Figure 4C:
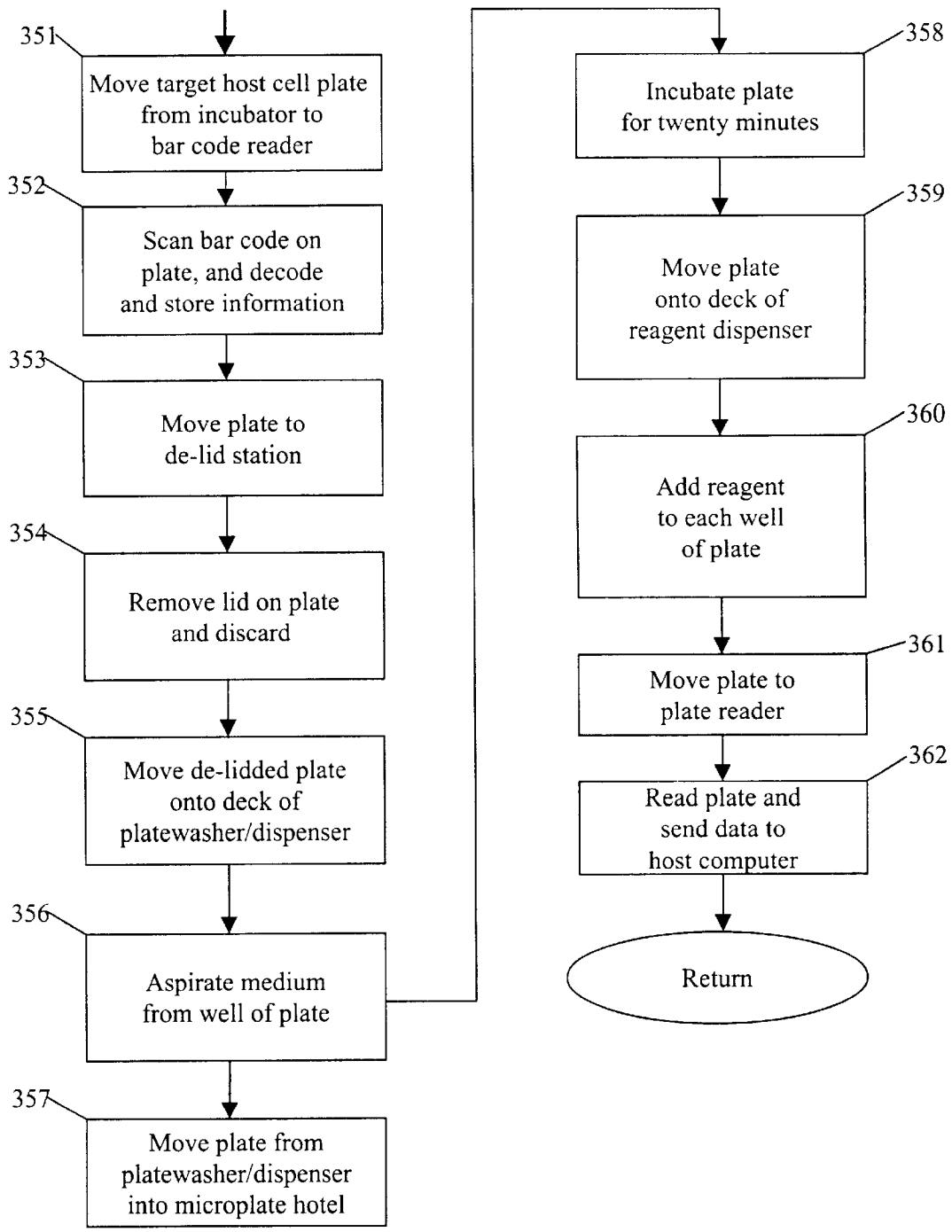
FIG. 4C shows a flow chart of a plate reading process performed by the Plate Reading Apparatus shown in FIG. 4B.

As further described below in connection with FIG. 4C, after the system is initialized, incubator shelves which contain the target host cell plates from the Infection Apparatus are transferred directly into incubators 303 of the Plate Reading Apparatus. Lyse and luciferase substrate reagents are loaded into reagent dispenser 305 then primter via the user interface. Execution of the Plate Reading Apparatus is then started and continues until all samples have been processed.

A plate reading process 350 which is performed by the Plate Reading Apparatus may include all or a combination of the steps described below in connection with FIGS. 4C. The steps may be scheduled in a manner that would be known to one skilled in the art to optimize efficiency, when and as required.

In step 351, robotic arm 301 removes a target host cell plate from incubators 303, and then delivers the plate to bar code reader 308. In step 352, bar code reader 308 reads the bar code on the label attached to the target host cell plate and the information is decoded and stored in electronic data files.

Next, robotic arm 301 delivers the target host cell plate to de-lid station 306 in step 353. De-lid station 306 removes and then discards the lid from the plate in step 354. The robotic arm places the de-lidded plate onto the deck of platewasher and dispenser 304 in step 355. In step 356, The platewasher and dispenser aspirates the medium from each well of the plate, followed by addition of a cell lysing reagent.

Robotic arm 301 then removes the target host cell plate from platewasher and dispenser 304 and places it into microplate hotel 309 in step 357. After the plate is incubated for 20 minutes in step 358, the plate is removed by the robotic arm and placed onto the deck of reagent dispenser 305 in step 359. The reagent dispenser then adds reagent to each well of the plate in step 360.

Next, robotic arm 301 moves the target host cell plate to plate reader 307 in step 361. The plate reader reads the plate and sends data electronically to the host computer in step 362.

The Plate Reading Apparatus may utilize a quick read method, which doesn't require a 20 minute incubation time. The order in which plates are processed, volumes dispensed and times utilized to read or incubate plates are configurable by the user and require no substantive changes to hardware or software.

The Plate Reading Apparatus may track plates by bar code. There is no need to place the target host cell plates in any particular order. A processing log is automatically generated which specifies when and how tasks were performed, any errors that occurred and the operator information required for validation of the system in a regulated environment.

The Plate Reading Apparatus may be equipped for remote access via a modem or web browser for monitoring system status. A signaling light changes color based on the status; red denotes an error, yellow denotes the system is processing samples and green means the system is idle. Dial out functionality allows the system to contact the operator via pager and/or e-mail in the case of an error.

In the embodiment of the automated system which is described above, the Transfection, Infection and Plate Reading Apparatuses are described as separate and distinct devices. They may, however, share components. For example, one robotic arm may be shared by the three Apparatuses. The sharing of the one robotic arm (or other components) by the three apparatuses may affect throughput. In order to minimize throughput reduction, the shared component must be scheduled for use in the most efficient manner possible. Further, the configuration of the Apparatuses may also be optimized to facilitate sharing of the component.

System alarm devices are installed on each apparatus. These devices may comprise, for example, a three colored light and an audible alarm. The three colored light is green when the system is idle, yellow when in operation and red if an error occurs. The audible alarm would sound when a system error occurs that requires operator intervention. The host computer controls the changing states of each of these devices.

Although commercially available components may be used in the above-described examples of the systems and methods of the present invention, the scope and spirit of the invention would remain applicable even if equivalent components, customized or otherwise, are used.

Other improvements and modifications which become apparent to persons of ordinary skill in the art after reading this disclosure, the drawings and the appended claims are deemed within the spirit and scope of the present invention.

What is claimed is:

1. A Transfection Apparatus in an automated system for performing antiviral drug susceptibility and resistance testing, comprising:

a robotic arm and a robotic arm controller which positions said robotic arm;

a system controller communicating with said robotic arm controller to control movement of said robotic arm, said system controller having a user interface for a user to design, schedule, optimize and monitor operation of said Transfection Apparatus; and a liquid handler introducing a resistance test vector comprising a patient-derived segment and an indicator gene into a host cell, a host cell plate containing the host cell being moved by said robotic arm to and from said liquid handler under a control of said system controller.

2. An Infection Apparatus in an automated system for performing antiviral drug susceptibility and resistance testing, comprising:

a robotic arm and a robotic arm controller which positions said robotic arm;

a system controller communicating with said robotic arm controller to control movement of said robotic arm, said system controller having a user interface for a user to design, schedule, optimize and monitor operation of said Infection Apparatus; and a pipettor harvesting viral supernatants from host cells in a packaging host cell plate, and introducing the viral supernatants into target host cells in a target host cell plate, the packaging host cell plate and target host cell plate being moved by said robotic arm to and from said pipettor under a control of said system controller.

3. A Plate Reading Apparatus in an automated system for performing antiviral drug susceptibility and resistance testing, comprising:

a robotic arm and a robotic arm controller which positions said robotic arm;

a system controller communicating with said robotic arm controller to control movement of said robotic arm, said system controller having a user interface for a user to design, schedule, optimize and monitor operation of said Plate Reading Apparatus;

a platewasher/dispenser for aspirating media from cells in a target host cell plate having a plurality of wells and adding a lysing reagent to at least one of said plurality of wells of the target host cell plate; and a luminometer measuring expression of an indicator gene in the target host cells in the target host cell plate processed by said platewasher/dispenser, wherein the target host cell plate is moved to and from said platewasher/dispenser and to and from said luminometer by said robotic arm under a control of said system controller.

4. An automated system for performing antiviral drug susceptibility and resistance testing, comprising:

a robotic arm and a robotic arm controller which positions said robotic arm;

a system controller communicating with said robotic arm controller to control movement of said robotic arm, said system controller having a user interface for a user to design, schedule, optimize and monitor operation of said system;

a Transfection Apparatus introducing a resistance test vector comprising a patient-derived segment and an indicator gene into a host cell in a host cell plate, under control of said system controller;

an Infection Apparatus harvesting viral supernatants from host cells in the host cell plate prepared by said Transfection Apparatus and introducing the viral supernatants into target host cells in a target host cell plate, under control of said system controller; and a Plate Reading Apparatus having a luminometer that measures expression of an indicator gene in the target host cells in the target host cell plate prepared by said Infection Apparatus, under control of said system controller, wherein the host cell plate and the target host cell plate are moved to, from and within said Transfection Apparatus, said Infection Apparatus and said Plate Reading Apparatus by said robotic arm under control of said system controller.

5. The automated system of claim 4 wherein antiviral drugs are added to the host cell plates by said Transfection Apparatus.

6. The automated system of claim 4 wherein said Transfection Apparatus includes a bar code scanner for scanning bar code labels applied to the host cell plates.

7. The automated system of claim 4 wherein said Transfection Apparatus processes samples according to a worklist.

8. The automated system of claim 4 wherein the host cell plates processed by said Transfection Apparatus include 96 well and/or 384 well type plates.

9. The automated system of claim 4 wherein antiviral drugs are added to the target host cell plates by said Infection Apparatus.

10. The automated system of claim 4 wherein the viral supernatants are harvested by said Infection Apparatus with filtration.

11. The automated system of claim 4 wherein the target host cell plates processed by said Infection Apparatus include 96 well and/or 384 well type plates.

12. The automated system of claim 4 wherein the target host cell plates are incubated for one minute after addition of the lyse reagent.

13. The automated system of claim 4 wherein the luciferase substrate is added by the luminometer.

14. The automated system of claim 4 wherein a plate lid is added and removed by a robot.

15. The automated system of claim 4 wherein bar code labels applied to the plates are used to track the plates through the system.

16. A transfection process in an automated system, which has a robotic arm, a system controller and a liquid handler, for performing antiviral drug susceptibility and resistance testing, comprising the steps of:

controlling said robotic arm to deliver a host cell plate containing a host cell to said liquid handler; and sending a signal from said system controller to said liquid handler to control said liquid handler to introduce a resistance test vector comprising a patient-derived segment and an indicator gene into the host cell.

17. An infection process in an automated system, which has a robotic arm, a system controller and a pipettor, for performing antiviral drug susceptibility and resistance testing, comprising the steps of:

controlling said robotic arm to deliver a packaging host cell plate to said pipettor;

controlling said robotic arm to deliver a target host cell plate to said pipettor; and sending a signal from said system controller to said pipettor to control said pipettor to harvest viral supernatants from host cells in the packaging host cell plate and to introduce the viral supernatants into target host cells in the target host cell plate.

18. A plate reading process in an automated system, which has a robotic arm, a system controller, a platewasher/dispenser and a luminometer, for performing antiviral drug susceptibility and resistance testing, comprising the steps of:

controlling said robotic arm to deliver a target host cell plate to said platewasher/dispenser;

sending a signal from said system controller to said platewasher/dispenser to control said platewasher/dispenser to aspirate media from cells in the target host cell plate and to add a lysing reagent to the wells of the target host cell plate;

controlling said robotic arm to deliver the target host cell plate processed by said platewasher/dispenser to said luminometer; and sending a signal from said system controller to said luminometer to control said luminometer to measure expression of an indicator gene in the target host cells in the target host cell plate.

* * * * *